Figure 1:
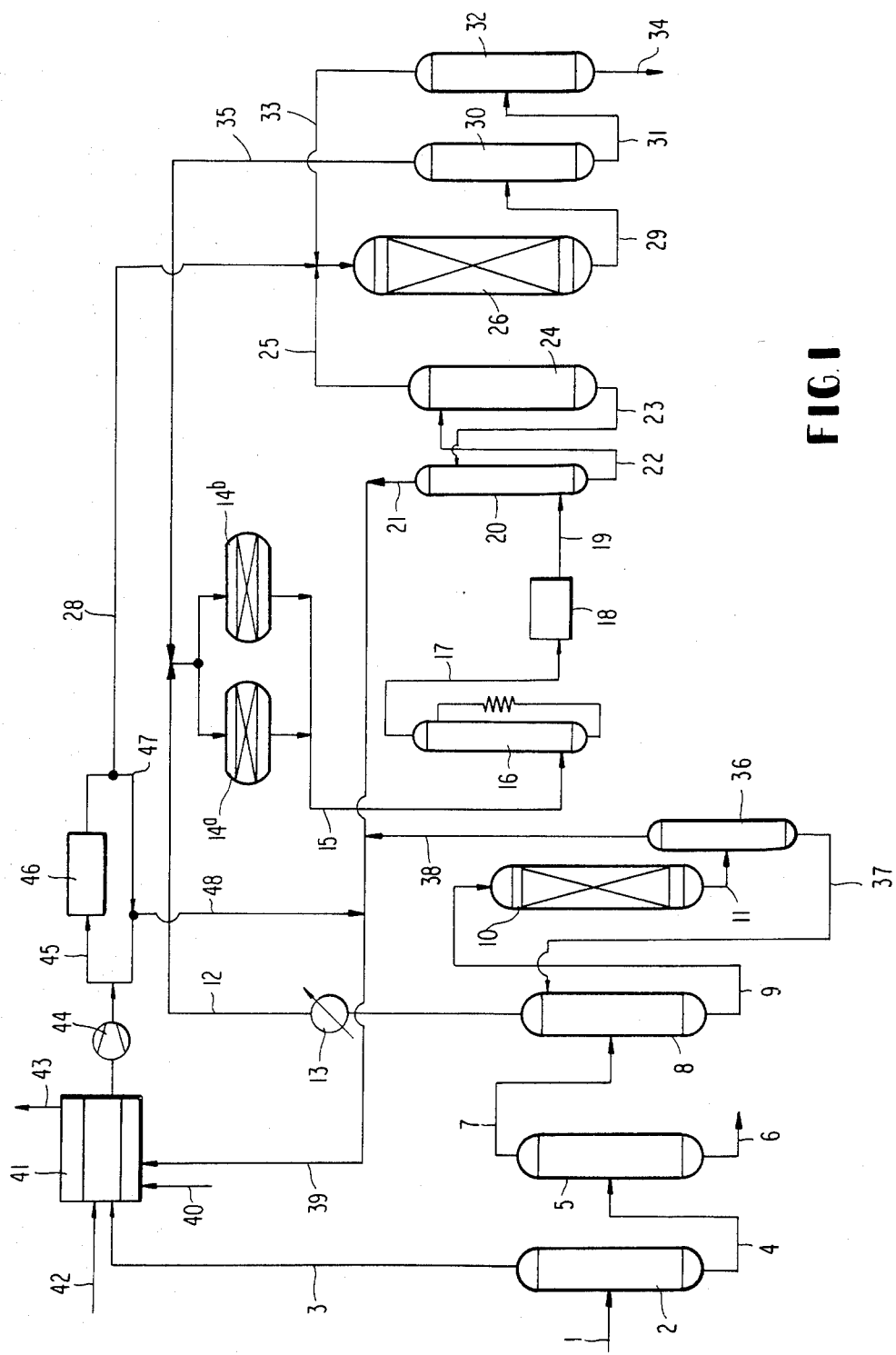

United States Patent [19]

Al-Muddarris

[11] Patent Number: 4,503,264

[45] Date of Patent: * Mar. 5, 1985

[54] PROCESS FOR THE MANUFACTURE OF METHYL TERT.-BUTYL ETHER

[75] Inventor: Ghazi R. Al-Muddarris, Cologne, Fed. Rep. of Germany

[73] Assignee: Davy McKee AG, Frankfurt, Fed. Rep. of Germany

[*] Notice: The portion of the term of this patent subsequent to May 11, 1999 has been disclaimed.

[21] Appl. No.: 408,207

[22] Filed: Aug. 16, 1982

Related U.S. Application Data

[63] Continuation of Ser. No. 216,683, Dec. 15, 1980, abandoned.

[30] Foreign Application Priority Data

Jul. 24, 1980 [DE] Fed. Rep. of Germany ....... 3027965

[51] Int. Cl.$^3$ .................................. C07C 41/05
[52] U.S. Cl. ................................ 568/697; 518/712; 518/728; 518/704
[58] Field of Search ............... 568/697; 518/712, 728, 518/704

[56] References Cited

U.S. PATENT DOCUMENTS

| | | | |
|---|---|---|---|
| 3,598,527 | 8/1971 | Quartulli et al. | 518/704 X |
| 3,940,428 | 2/1976 | Connell et al. | 518/704 |
| 3,962,300 | 6/1976 | Hiller et al. | 518/704 X |
| 4,118,425 | 10/1978 | Herbstman | 568/697 |
| 4,329,516 | 5/1982 | Al-Muddarris | 568/697 |

OTHER PUBLICATIONS

Choudhary, Chem. Ind. Dev., vol. 8 (1974) 32–41.
Heck et al., Hydrocarbon Processing (1980) 185–191.
Reynolds et al., The Oil & Gas Journal, Jun. 16, 1975, 50–52.
Pallay et al., Hydrocarbon Processing (1976) 121–125.
Pecci et al., Hydrocarbon Processing (1977) 98–102, 186.

*Primary Examiner*—Bernard Helfin
*Attorney, Agent, or Firm*—Bernard, Rothwell and Brown

[57] ABSTRACT

A process is disclosed for producing methyl tert.-butyl ether wherein n-butane is isomerized to isobutane which is then catalytically dehydrogenated to form an isobutane/isobutene mixture, while natural gas is reformed to form synthesis gas containing CO and $H_2$ which is in turn converted to methanol, the resulting methanol and isobutene in the isobutane/isobutene mixture being etherified to form methyl tert.-butyl ether. Isobutane is then separated from the resulting etherification mixture and is recycled to the dehydrogenation stage. Secondary product gases from at least one of the isomerization, dehydrogenation and methanol synthesis stages are combusted and used to produce superheated steam at high pressure which is expanded to a medium pressure by expansion through at least one first backpressure turbine coupled to a corresponding compressor or compressors for compression of at least one of the synthesis gas and of the dehydrogenation product gas, while resulting medium pressure steam is expanded in turn through at least one second back-pressure turbine to low pressure steam in excess of atmospheric pressure, such low pressure steam being utilized for heating process apparatus.

13 Claims, 2 Drawing Figures 4,503,264

PROCESS FOR THE MANUFACTURE OF METHYL TERT.-BUTYL ETHER

This is a continuation of application Ser. No. 216,683 filed Dec. 15, 1980, and now abandoned.

This invention relates to a process for the manufacture of methyl tert.-butyl ether.

Since it is specified in a number of countries that lead-free gasoline or gasoline having a reduced lead content has to be used, it has been necessary to investigate other gasoline additives with regard to their suitability for improving the octane number. Among these additives, methyl tert.-butyl ether assumes a priority position because of its high octane number (octane number between 115 and 135). It is possible for the gasoline fraction from a given quantity of crude oil to be increased by the use of a methyl tert.-butyl ether additive, since other components with a low octane number, such as straight-run distillates, can remain in the gasoline. Furthermore, the quantity of the costly aromatic substances, which otherwise are necessary for improving the octane number, can be reduced.

Previously, the isobutene used in connection with the manufacture of methyl tert.-butyl ether originated almost exclusively from the cracking of hydrocarbons. However, the amount of isobutene which is available from this source is limited. The available quantity of isobutene could be increased by the isomerization of the n-butenes in the $C_4$-cut of the hydrocarbon cracking. However, commercial processes for this purpose have not as yet been available in practice.

On the other hand, butanes are available in large quantities at the time of crude oil production or as liquid petroleum gas. It is possible from these sources for isobutane either to be separated or produced by isomerization of n-butane, which is then capable of being converted to isobutene by dehydrogenation. Consequently, with the liquefied petroleum gas (LPG), there is available in large quantities a row or initial product which has so far been used only to an insufficient extent at the locations where crude oil is produced.

It is known from German Offenlegungsschrift 2620011 to process a flow of n-butane occurring in the natural oil refinery into methyl tert.-butyl ether. In this process, the n-butane is partially isomerized to isobutane and the mixture of n-butane and isobutane is then partially dehydrogenated. As a result of the dehydrogination, n-butenes are formed as well as isobutene. The dehydrogenation product still containing n-butane is then etherified with an alcohol excess, more especially with methanol, the formed isobutene thereby being converted into methyl tert.-butyl ether. The excess methanol is extracted from the product mixture with water and the remaining $C_4$ hydrocarbons are separated by distillation from the ether and returned to the dehydrogenation stage. Because of the presence of n-butane which is necessary with this process, it is necessary to have an installation of correspondingly larger dimensions for a given production output of methyl tert.-butyl ether. Moreover, as a result of the return of $C_4$ hydrocarbons containing n-butene into the dehydrogenation stage, butadiene is also formed and this can lead to disruptions in the plant or installation. Finally, the separation of methanol from the etherification mixture by extraction with water is also disadvantageous, because the methanol has to be recovered from the aqueous phase and the ether has to be dried.

For the purpose of obviating the aforementioned defects, it has already been proposed to dehydrogenate an isobutane which is substantially free from n-butane and to effect the etherification with a dehydrogenated mixture consisting essentially only of isobutene and isobutane. Subsequently, from the etherification product, first of all the isobutane and thereafter the excess methanol are separated by distillation.

It is the object of the present invention to improve the thermal efficiency of the manufacture of methyl tert.-butyl ether from a flow of n-butane, i.e. to reduce the amount of energy which has to be supplied from outside to a plant for making methyl tert.-butyl ether from n-butane, and more especially that energy supplied as electrical energy.

According to the invention, there is provided a process for the manufacture of methyl tert.-butyl ether which comprises isomerizing n-butane to form isobutane, catalytically dehydrogenating the resulting isobutane to form an isobutane/isobutene mixture, steam reforming natural gas to form a synthesis gas containing CO and $H_2$, converting resulting synthesis gas to methanol, etherifying resulting methanol with isobutene in the isobutene/isobutane mixture to form methyl tert.-butyl ether, separating isobutane from the etherification mixture, recycling separated isobutane to the dehydrogenation stage, burning secondary product gases from at least one of the isomerization, dehydrogenation and methanol synthesis stages, superheating steam at high pressure by heat exchange with the resulting hot combustion gases, expanding resulting high pressure steam to a medium pressure in at least one first back-pressure turbine coupled to a corresponding compressor or compressors for the compression of at least one of the synthesis gas and of the dehydrogenation product gas, supplying part of resulting medium pressure steam as process steam to the steam reforming stage, expanding another part of said medium pressure steam in at least one second back-pressure turbine to a low pressure in excess of atmospheric pressure, and utilizing resulting low-pressure steam for heating process apparatus.

Preferably the high pressure steam is produced at a pressure in the range of from about 90 bar to about 120 bar, whilst the medium pressure steam may be produced at a pressure in the range of from about 15 bar to about 45 bar and the low pressure steam may be produced at a pressure in the range of from about 3 bar to about 8 bar.

By using the teachings of the invention, it is possible to achieve a thermal efficiency of the entire process of greater than 60%. The efficiency $\eta$ in % is in this case defined as follows:

$$\eta = \frac{\text{heat capacity of the products}}{\text{heat capacity of the initial materials and fuels}} \times 100,$$

the heat capacities being calculated from the mean quantitative flows of the substances and their lower calorific values and the fuels also having incorporated thereinto the fuel equivalent for the generation of the electrical energy which is supplied. It has surprisingly been found that a considerable improvement in the power/heat economy is produced with the coupling of the reforming and methanol synthesis into the overall process, if the secondary product gases being formed in total are utilized for the production of high pressure superheated steam, which then serves in two stages in back-pressure turbines for the delivery of power and at the same time process steam is made available for the reforming operation under the required medium pressure. In this manner, an essential part of the compression energy necessary in the overall process is provided from the low-value secondary product gases. In addition, after the expansion stage, low-pressure steam is available for the heating of process apparatus, more especially distillation columns in the separate processing steps, and also for flushing the dehydrogenation reactors prior to the regeneration. By means of the process according to the invention, and thanks to the reforming and methanol synthesis integrated into the complete process, a substantial portion of the energies necessary in the separate stages is thus made available internally and utilized. By the coupling of the reforming/methanol synthesis, an improvement in the efficiency as defined above and decisive as a whole for the economic production of methyl tert.-butyl ether from liquefied petroleum gas is thus produced as compared with a process with which the reforming and methanol synthesis are not integrated.

In accordance with a preferred process according to the present invention, provision is made for the secondary product gases to be burnt in the combustion chamber of the reformer furnace and for the superheated steam to be generated with the combustion gases discharging from the combustion chamber. With this form of the process according to the present invention, the combustion products of the secondary product gases first of all supply the heat which is necessary for the steam reformation of hydrocarbons to synthesis gas. The combustion chamber of the reformer furnace is particularly suitable for the combustion of the secondary product gases since a sufficient space is available for the combustion or burning of the gases of heterogeneous composition, which gases contain considerable amounts of $C_3$- and $C_4$-hydrocarbons and also methanol and dimethyl ether in addition to methane and hydrogen. In addition, the combustion of these components is promoted by the high-alloy steels of the reformer tubes around which the combustion gases circulate. The combustion gases which discharge from the combustion chamber are then utilized in a waste heat boiler for the production of the superheated, high-pressure steam.

It is also possible for superheated, high-pressure steam for driving the first back-pressure turbine or turbines to be additionally produced by combustion of hydrocarbon gas, more especially of natural gas. This generation of steam is expediently effected separately from the production of steam with the secondary product combustion gas. Both steam generators supply their steam to the same high-pressure steam line, from which the first back-pressure turbine or turbines are fed.

Preferably the compressors of the cycle gases of the methanol synthesis stage and of the isomerization stage are driven by the second back-pressure turbines. In addition, the medium-pressure steam can serve for the driving of turbines coupled to additional blowers and pumps.

Medium-pressure steam is expediently produced by heat exchange with the combustion gases being formed with the regeneration of the dehydrogenation catalyst. As is known, during the regeneration, the coke deposited on the catalyst during the reaction is burnt off with air, a combustion gas at, for example, 500° to 550° C., being formed. This hot combustion gas serves for the production of medium pressure saturated steam in a special waste-heat boiler. This saturated steam can, for example, be used for heating process apparatus if, for this purpose, higher temperatures than those available in the low-pressure steam are necessary. By way of example, this saturated steam may serve for heating the distillation column for the separation of the methanol/methyl tert.-butyl ether azeotrope from the pure ether.

It is additionally preferably provided for the higher alcohols formed as by-products in the synthesis of methanol to also be supplied to the combustion stage. These higher alcohols, mainly isobutanol, are present in admixture with aqueous methanol. In this manner, a secondary product is eliminated, the working up of which is uneconomical.

Provision can additionally be made for hydrogen to be separated from at least a part of the secondary product gas from the methanol synthesis stage, advantageously from at least a part of the purge gas from the synthesis gas loop, for the hydrogen to be used in the isomerization of the n-butane, and for the secondary product gas now impoverished with regard to hydrogen to be supplied to the combustion stage.

Figure 2:
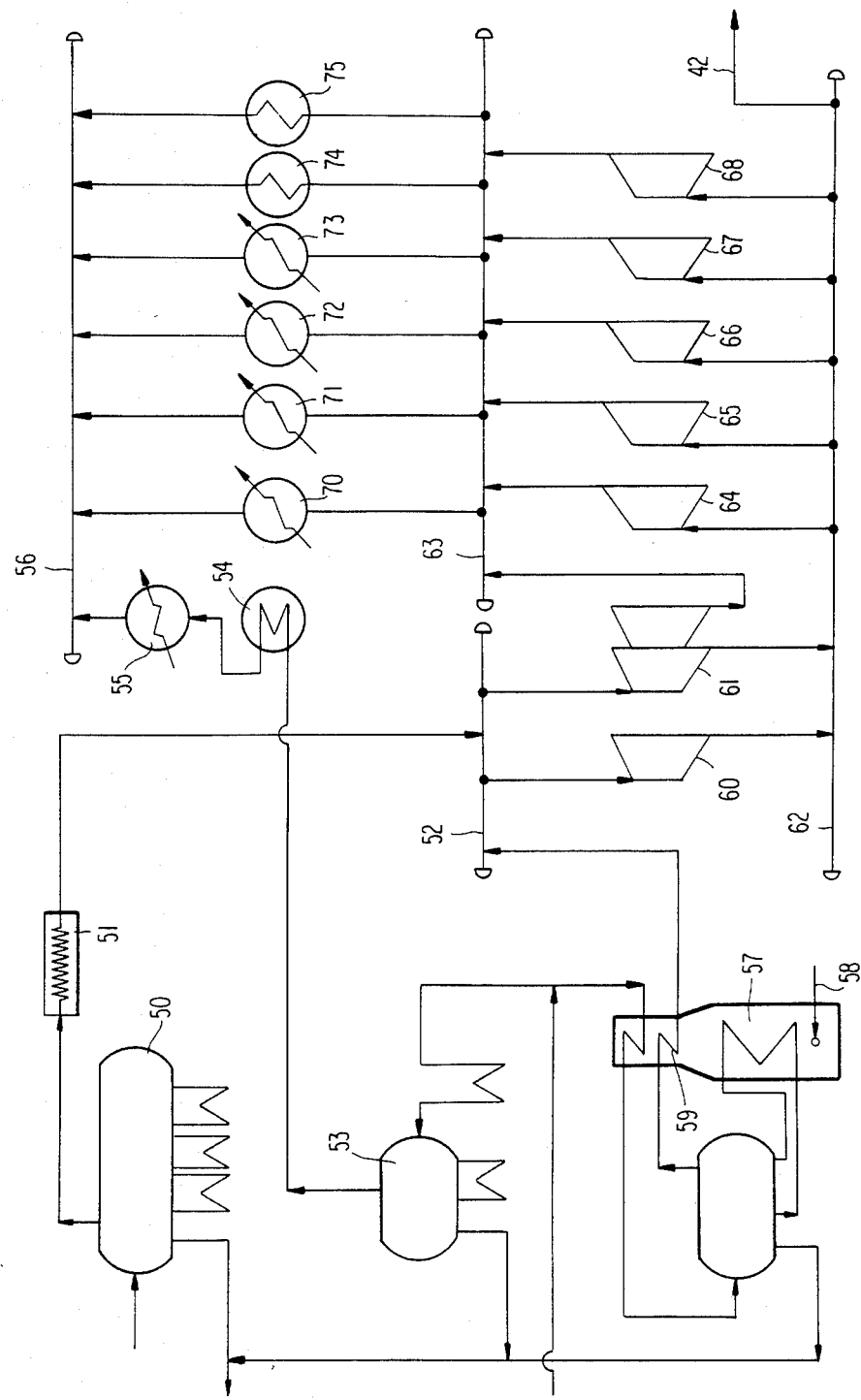

In order that the invention may be readily understood and carried into effect, a preferred form of plant operating according to the process of the invention will now be described, by way of example only, with reference to the accompanying drawings, wherein:

FIG. 1 is the flow diagram of an installation for carrying the process according to the invention into effect; and FIG. 2 is the steam flow diagram of an installation for carrying out the process of the invention.

Referring now to FIG. 1 of the drawings, a mixture of light hydrocarbons, such as the gas mixture formed upon the separation of crude oil by distillation, is supplied by way of pipe 1 to rectifier or stripping column 2. The gas mixture is separated by distillation into a $C_{1-3}$ flow and a $C_{4+}$ flow. The $C_{1-3}$ flow passing overhead serves as starting material for the methanol synthesis and is supplied by way of pipe 3 to reformer furnace 41. The bottom fraction, consisting of $C_4$ and heavier hydrocarbons, passes through pipe 4 to column 5 in which the $C_4$ fraction is distilled overhead and $C_5$ and higher hydrocarbons are extracted through pipe 6 as bottom product. The $C_4$ fraction, which consists essentially of n-butane, passes through pipe 7 to the de-isobutanization column 8, in which a separation of the total supply into isobutane and n-butane takes place. The n-butane is drawn off as bottom product through pipe 9 and is supplied to catalytic isomerization reactor 10 in which the n-butane is partially isomerized to isobutane by passage, for example, over a platinum-containing catalyst at 150° to 200° C. The isobutane/n-butane mixture is extracted from the reactor 10 through pipe 11 and is freed in a depropanization column 36 from $C_{1-3}$ hydrocarbons, which are discharged overhead by way of pipe 38. The bottom product of the column 36, which product consists essentially of isobutane and n-butane, passes by way of pipe 37 back again to the de-isobutanization column 8.

The high-percentage isobutane fraction leaves deisobutanization column 8 as head product through pipe 12, is heated in heat exchanger 13 and, after expansion and being combined with isobutane returned by way of pipe 35, is fed into catalytic dehydrogenation reactors 14a and 14b. Reactors 14a and 14b are charged alternately with the stream of isobutane, the reactor switched off at any time being regenerated with hot air and the coke which is deposited on the catalyst being burnt off. The dehydrogenation takes place on a chromium oxide/aluminium oxide catalyst at temperatures in the range of from about 540° C. to about 640° C. The product gas from the dehydrogenation reactor consists essentially of an isobutene/isobutane mixture and passes by way of pipe 15 to quenching tower 16, in which the mixture is quenched or chilled by direct contact with cold oil. Instead of quenching tower 16, it is also possible for an indirect heat exchange to take place with the cold stream of isobutane flowing to the dehydrogenation reactors. The cooled isobutene/isobutane mixture then flows through pipe 17 to multi-stage compressor 18 with intermediate cooling, by means of which the pressure of the mixture is raised, for example, to about 12 bar. The mixture then travels by way of pipe 19 into absorption column 20 in which isobutene and isobutane are washed out of the gas flow with absorption oil. Hydrogen and light hydrocarbons which are formed as secondary product of the dehydrogenation remain in the gas phase and leave the column overhead through pipe 21. The cold absorption oil charged with isobutene and isobutane then passes by way of pipe 22 into desorber 24 in which the $C_4$ hydrocarbons are driven off by heating the absorption solution. The absorption oil as thus regenerated flows back through pipe 23 into absorber 20. The gas mixture, consisting essentially of isobutene and isobutane, leaves desorber 24 by way of pipe 25.

The secondary product gases discharged from columns 20 and 36 through the pipes 21 and 38, respectively, are combined with the purge gas from the methanol synthesis loop from pipe 48 and supplied by way of pipe 39 to the combustion chamber of reformer furnace 41 where they are burnt off with air 40. The heat of the hot flue gases discharging at 43 is utilized in a steam boiler installation for generating superheated high-pressure steam, as is hereinafter more fully described. In reformer furnace 41, the $C_{1-3}$ hydrocarbons supplied through pipe 3 are converted by means of the steam supplied by pipe 42 into synthesis gas which, after having been compressed in compressor 44, is delivered by pipe 45 to synthesis reactor 46 in which the formation of methanol occurs in the presence of a catalyst. The formed methanol is removed by condensation from the reaction gas. The residual synthesis gas is pumped back by way of pipe 47/45 into synthesis reactor 46, after a small portion of the gas has been discharged from the synthesis gas circuit through pipe 48 and has likewise been delivered into header pipe 39 to the combustion chamber of reformer furnace 41.

The isobutene/isobutane mixture is fed, together with the methanol supplied through pipe 28 and methanol/ether mixture returned through pipe 33 and after preheating (not shown) into catalytic etherification reactor 26. Reactor 26 contains a solid bed catalyst and cooling means for dissipating the heat of reaction. In reactor 26, the isobutene introduced by way of pipe 25 is reacted with the methanol to form methyl tert.-butyl ether. A mixture consisting essentially of methyl tert.-butyl ether, isobutane and excess methanol leaves reactor 26 and is supplied by way of pipe 29 to first pressurized column 30. In column 30, the isobutane is distilled off overhead and is combined by way of pipe 35 with the feed stream for dehydrogenation reactors 14a and 14b. The sump product of column 30 is a mixture of methyl tert.-butyl ether and methanol and is fed by way of pipe 31 to a second pressurized column 32 in which an azeotrope consisting of methanol and methyl tert.-butyl ether is distilled overhead, the azeotrope returning by way of pipe 33 into the etherification reactor 26. The methyl tert.-butyl ether is drawn off as product from the sump of column 32 at pipe 34.

In FIG. 2, reference numeral 50 indicates the stream drum of the waste-heat boiler which is connected on the output side of reformer furnace 41 and in which high-pressure steam is produced from the hot combustion gases of the secondary products. This high-pressure steam, which is available from steam drum 50, for example, at 109 bar and 318° C., is superheated in superheater 51, for example, to 482° C. and delivered to high-pressure steam line 52. Waste-heat boiler 53, which is on the output side of the dehydrogenation reactors and in which the heat of the flue gases being formed with the catalyst regeneration and at a temperature, for example, of 540° C., is utilized for producing medium pressure steam. With the embodiment as represented, this saturated steam serves initially for heating reboiler 54 of column 32 and then for heating the isobutene/isobutane mixture in heat exchanger 55 before entry into etherification reactor 26. As a result, the steam condenses, and the condensate is delivered to condensate line 56. Finally, there is also provided steam boiler 57 which is fired with natural gas by way of pipe 58 and supplies high-pressure steam which is superheated in superheater 59 and is delivered to high-pressure steam line 52.

Two back-pressure turbines 60 and 61 are charged with steam from high-pressure steam line 52. Turbine 60 drives synthesis gas compressor 44, with which the reformed gas is compressed in several stages from, for example, 16 bar up to, for example, 94 bar. The waste steam of turbine 60 is fed as superheated steam below about 30 bar into medium pressure line 62. Turbine 61, likewise charged with high-pressure steam, is designed as a back-pressure bleeder turbine. It drives the compressors for the compression of the product gas from the dehydrogenation reactors 14a and 14b, from a pressure of, for example, ⅓ bar to a pressure of about 12 bar, under which the absorption of the isobutene/isobutane mixture takes place in the column 20. The high-pressure steam used for charging turbine 61 is in this case partially expanded to the medium pressure and is delivered to the line 62, is partially expanded to low pressure, e.g. 5.5 bar and then delivered to low-pressure steam line 63.

A series of turbines 64–68 is charged from medium pressure steam line 62, these turbines serving to drive additional compressors and blowers. Turbine 64 drives the synthesis gas recycle compressor (not shown in FIG. 1) which is disposed in the synthesis gas loop 45–47. Turbine 65 drives the compressor for the gas recycled through isomerization reactor 10. Turbine 66 drives the blower for the flue gas from the waste-heat boiler (steam drum 50) connected on the output side of reformer furnace 41. Turbine 67 drives the blower for drawing in the air for combustion, which is supplied by way of pipe 40 to the combustion chamber reformer furnace 41, while turbine 68 drives the charging pump of isomerization reactor 10. In addition, other turbines for driving pumps may operate between lines 62 and 63, but these are not represented in FIG. 2 for the purpose of simplicity. Finally, from medium pressure steam line 62, process steam is supplied by way of pipe 42 to reformer furnace 41.

By means of the low-pressure steam which has, for example, a temperature of 190° C. and a pressure of 5.5 bar, numerous processing apparatus, more particularly the reboilers of different columns, are heated, the steam being condensed and delivered to condensate line 56. Consequently, reboiler 70 serves for heating the depropanization column 36, reboiler 71 for heating the deisobutanization column 8, reboilers 72 and 73 for heating the methanol pre-purification column and the methanol fine-purification column, respectively. Heat exchanger 74 serves for the supply of heat in the sump of column 20 and heat exchanger 75 for the supply of heat in the sump of column 30.

It is claimed:

1. A process for the manufacture of methyl tert.-butyl ether which comprises isomerizing n-butane to form isobutane in an isomerization stage, catalytically dehydrogenating resulting isobutane in a dehydrogenating stage to form an isobutane/isobutene mixture, steam reforming natural gas to form a synthesis gas containing CO and $H_2$ in a steam reforming stage, converting the resulting synthesis gas to methanol in a methanol synthesis stage, etherifying the resulting methanol with isobutene in the isobutene/isobutane mixture to form methyl tert.-butyl ether in an etherification mixture, separating isobutane from the etherification mixture, recycling separated isobutane to the dehydrogenation stage, burning secondary product gases from at least one of the isomerization, dehydrogenation and methanol synthesis stages in a combustion stage to form hot combustion gases, generating and superheating steam at high pressure by heat exchange with the resulting hot combustion gases, expanding at least a part of the resulting high pressure steam to a medium pressure in first back-pressure turbines coupled to compressors for the compression of the synthesis gas and of the dehydrogenation stage product gas, supplying part of resulting medium pressure steam as process steam to the steam reforming stage, expanding another part of said medium pressure steam in second back-pressure turbines to low pressure steam in excess of atmospheric pressure, and utilizing resulting low pressure steam for heating apparatus employed in said process for the manufacture of methyl tert.-butyl ether.

2. A process according to claim 1, in which the high pressure steam is produced at a pressure in the range of from about 90 bar to about 120 bar.

3. A process according to claim 1, in which the medium pressure steam is produced at a pressure in the range of from about 15 bar to about 45 bar.

4. A process according to claim 1, in which the low pressure steam is produced at a pressure in the range of from about 3 bar to about 8 bar.

5. A process according to claims 2,3 or 4, in which the secondary product gases are burnt in the combustion chamber of a reformer furnace in which the steam reforming stage is carried out and in which resulting combustion gases are used to generate superheated steam at high pressure.

6. A process according to claim 1, in which the high pressure steam is produced at a pressure in the range of from about 90 bar to about 120 bar, in which the medium pressure steam is produced at a pressure of from about 15 bar to about 45 bar, and in which the low pressure steam is produced at about 3 bar to about 8 bar.

7. A process according to claim 1 or claim 6, in which additionally superheated steam at high pressure for driving said first back-pressure turbines is generated by combustion of natural gas.

8. A process according to claim 1 or claim 6, in which the secondary product gases are burnt in the combustion chamber of a reformer furnace in which the steam reforming stage is carried out, in which resulting combustion gases are used to generate superheated steam at high pressure, and in which additional superheated steam at high pressure for driving said at least one first back-pressure turbine is generated by combustion of natural gas.

9. A process according to claim 1 or claim 6, in which each of the second back-pressure turbines is coupled to a respective compressor selected from a methanol synthesis recycle compressor and an isomerization gas recycle compressor.

10. A process according to claim 1 or claim 6, in which medium pressure steam is generated by heat exchange with combustion gases formed during regeneration of dehydrogenation catalyst of the dehydrogenation stage.

11. A process according to claim 1 or claim 6, in which higher alcohols formed as by-products in the methanol synthesis stage are supplied to the combustion stage.

12. A process according to claim 1, in which hydrogen is separated from at least a part of the secondary product gas from the methanol synthesis stage and is supplied to the isomerization stage and in which the secondary product gas impoverished with regard to hydrogen is supplied to the combustion stage.

13. A process according to claim 12, in which hydrogen is separated from purge gas from the methanol synthesis gas loop and is supplied to the isomerization stage.

* * * * *